(12) United States Patent
Lawless (10) Patent No.: US 8,207,508 B2
(45) Date of Patent: Jun. 26, 2012

(54) DEVICE AND METHOD FOR QUANTIFYING A SURFACE'S CLEANLINESS

(76) Inventor: John L. Lawless, Pacifica, CA (US)

( * ) Notice: Subject to any disclaimer, the term of this patent is extended or adjusted under 35 U.S.C. 154(b) by 574 days.

(21) Appl. No.: 12/399,973

(22) Filed: Mar. 8, 2009

(65) Prior Publication Data

US 2009/0223635 A1    Sep. 10, 2009

Related U.S. Application Data

(60) Provisional application No. 61/034,977, filed on Mar. 8, 2008.

(51) Int. Cl.
*G01J 1/58* (2006.01)
(52) U.S. Cl. .................. 250/458.1; 250/301
(58) Field of Classification Search ............ 250/458.1, 250/301
See application file for complete search history.

(56) References Cited

U.S. PATENT DOCUMENTS

| | | | | |
|---|---|---|---|---|
| 4,910,406 | A | * | 3/1990 | Craig et al. .................. 250/372 |
| 5,828,460 | A | * | 10/1998 | Lucovsky et al. ............ 356/446 |
| 6,310,348 | B1 | | 10/2001 | Melling et al. |
| 2003/0232448 | A1 | * | 12/2003 | Shelley et al. ................ 436/164 |
| 2005/0147533 | A1 | * | 7/2005 | Cole et al. ...................... 422/73 |

OTHER PUBLICATIONS

Transmittal, International Search Report and Written Opinion for PCT/US2009/036446, Sep. 29, 2009, 11 pages.
Chawla, "Measuring Surface Cleanliness," Precision Cleaning, pp. 11-15, Jun. 1997.

* cited by examiner

*Primary Examiner* — David Porta
*Assistant Examiner* — Hugh H Maupin
(74) *Attorney, Agent, or Firm* — Louis L. Wu (57) ABSTRACT

Provided are devices and methods for quantifying a surface's cleanliness relative to a contaminant. Such devices and methods may comprising and use a source of interrogating radiation to which the contaminant is responsive, a means for directing the interrogating radiation, a detector, and an analyzer. Radiation emitted from the source is directed by the radiation means toward the surface or a surface cleaner that may hold the contaminant. The detector detects radiation from the surface or the surface cleaner produced in response to the interrogating radiation by the contaminant, e.g., fluorescent or phosphorescent radiation, and generate a corresponding signal that is compared by the analyzer relative to an electronic standard that corresponds to the surface in an acceptably clean state so as to quantify the surface's cleanliness.

29 Claims, 5 Drawing Sheets

DEVICE AND METHOD FOR QUANTIFYING A SURFACE'S CLEANLINESS

CROSS REFERENCE TO RELATED APPLICATIONS

This application claims priority to U.S. Provisional Application Ser. No. 61/034,977, entitled "Device and Method for Quantifying a Surface's Cleanliness," filed on Mar. 8, 2008, by inventor John L. Lawless, the disclosure of which is hereby incorporated by reference in its entirety.

BACKGROUND

1. Technical Field

The present invention generally relates to devices and methods for quantifying a surface's cleanliness. In particular, the invention relates to such and methods that direct interrogating radiation toward a surface or a surface cleaner detecting radiation from the surface or the surface cleaner produced in response to the interrogating radiation.

2. Related Art

In numerous industries, surface contamination and measurement thereof are issues of utmost importance. For example, the manufacturing of painted metal articles may require metal parts to be cut before they are painted. Often, cutting processes leave oil residues on the metal parts. Oil residues may interfere with the adhesion of paint to the metal parts. Thus, as a quality control measure, the metal parts are typically cleaned after they are cut before they are painted to ensure that the paint does not peel away from the parts.

Surface purity is also an important issue in facilities that handle reactive chemicals. For example, after each run, cleanliness of pharmaceutical reactors must be validated before they are returned to use. Similarly, in environments that are repeatedly exposed to large quantities of fluorine, e.g., reaction chambers of chemical lasers that use hydrogen fluoride and/or deuterium fluoride, cleanliness is a critical issue since the fluorine compounds may be highly reactive in nature and may explode upon contact with contaminants.

Furthermore, exacting standards of surface cleanliness are required in various aerospace and astronautic applications. For example, space shuttles use large quantities of pure oxygen which explodes upon contact with hydrocarbon impurities. All surfaces exposed to pure oxygen must be cleaned to exacting standards. Similarly, many parts on modern airplanes and helicopters, particularly those made with epoxy composites, must be cleaned before they are bonded to each other. Otherwise, catastrophic results may occur due to adhesion failure.

In response to these concerns, various industries have come up with cleaning protocols and standards to assure address cleanliness issues. Both aerospace and semiconductor industries have found it essential to control contamination through the use of clean rooms. Clean room standards have now been adopted by the International Organization for Standardization (ISO) that set forth contamination per unit volume. As defined by ISO 14644-2, "class 100" means that there are less than 100 particles of 0.5 µm or larger in a cubic foot. In addition, standards have been developed that set forth contamination per unit surface area.

Nevertheless, there are a number of shortcomings associated with known protocols and standard methods for determining the cleanliness of a surface. For example, in nonvolatile residue (NVR) testing, a surface cleaner, e.g., a sheet of filter paper or (preferably non-shredding) tissue wipe, may be used to wipe down a surface. The cleaner may then be sent away to a NVR testing facility where it is washed with a suitable solvent to extract any contaminants the may be present on the tissue. Then, the solvent is left to evaporate in a preweighed weighing dish. The resulting added mass is reported in milligrams per square foot of surface area.

NVR testing is suboptimal for numerous reasons. In general, NVR testing is procedurally difficult. Such testing may also be time consuming. When the NVR testing facility is remotely located relative to the location of the surface to be tested, it may take days to receive results of such testing. To ensure that the surface does not become contaminated by the time NVR test results arrive, the surface may have to be isolated and stored in controlled environments such as clean rooms, thereby increasing the costs associated with cleanliness validation. Furthermore, such testing results occasionally in gross errors.

While in situ testing techniques are available, they are generally qualitative rather than quantitative in nature. For example, black-light (wavelength 366 nm) monitoring of large-scale bonding surface for contamination has been described in Chawla, "Measuring Surface Cleanliness," Precision Cleaning, pages 11-15, June, 1997 (accessed from http://www.p2pays.org/ref/02/01816.htm on Mar. 2, 2009, hereinafter "Chawla"). However, such techniques are accompanies with numerous limitations. In general, black light has not been known to be useful for detecting contaminants such as light machine and tapping oils, hydraulic oil and silicone room-temperature vulcanizer (RTV) compounds that do not fluoresce strongly at low levels of contamination. In addition, black-light inspection is subjective, not quantitative and creates no record that is analyzable relative to accepted electronic standards.

The few quantitative technologies that have been used to determine the cleanliness of a surface are generally limited in nature. For example, U.S. Pat. No. 6,310,348 to Melling et al. describes an accessory for an FTIR spectrometer comprises fiber-optic cables that may be used to detect and characterize quantifying thin films on reflective surfaces for cleaning validation applications. Such spectrometry based technologies require a reflective surface and the precision relative placement the accessories relative to the surface so as to achieve a "grazing angle" for maximum sensitivity.

Thus, opportunities exist to provide alternatives and improvements to known protocols and technologies for evaluating the cleanliness of a surface.

SUMMARY OF THE INVENTION

In a first embodiment, the invention provides devices for quantifying a surface's cleanliness relative to a contaminant. The devices of the invention include a source of interrogating radiation to which the contaminant is responsive, a means for directing the interrogating radiation, a detector, and an analyzer. Radiation emitted from the source is directed by the radiation means toward the surface or a surface cleaner that may hold the contaminant. The detector is positioned to detect radiation from the surface or the surface cleaner produced in response to the interrogating radiation by the contaminant, e.g., fluorescent or phosphorescent radiation. Once radiation is detected, the detector generates a signal that corresponds to the detected radiation. Optionally, the detector may further be responsive to radiation reflected from or transmitted by the surface or the surface cleaner. Then, the analyzer compares the signal from the detector relative to an electronic standard that corresponds to the surface in an acceptably clean state so as to quantify the surface's cleanliness.

In another embodiment, methods are provided for quantifying a surface's cleanliness relative to a contaminant. The methods involve generating interrogating radiation to which the contaminant is responsive. The interrogating radiation is directed toward the surface or a surface cleaner, e.g., a sheet of filter paper and/or a cleaning fluid, that may hold the contaminant from the surface. Radiation from the surface or the surface cleaner produced in response to the interrogating radiation by the contaminant is detected. In turn, a signal is generated that corresponds to the detected radiation. The signal from the detector is compared to a standard that corresponds to the surface in an acceptably clean state so as to quantify the surface's cleanliness. Optionally, the method may be used to quantify a surface's bondability relative to at least one bondability parameter, e.g., surface roughness.

In a further embodiment, a method is provided for bonding a plurality of surfaces that may or may not be contaminated by at least one surface contaminant. The method generally involves quantify the at least one surfaces' cleanliness using the above-described method and applying an adhesive between the surfaces so as to bond the surfaces.

The invention may be used to quantifying a surface's cleanliness relative to any of a number of contaminants using interrogating radiation of various wavelengths. For example, the surface contaminant may comprise particulate matter and/or organic matter such as a hydrocarbon. In addition, the interrogating radiation may be of ultraviolet, infrared and/or visible wavelengths. Monochromatic radiation and/or radiation including a range of wavelengths may be used.

Different types of hardware may be employed that suitable for handheld use. For example, the detector may include, a charge-couple device (CCD) camera and/or a photodiode. In addition, the analyzer may include a microelectronic device and/or a computer port interface. When the invention is used to quantify a surface's cleanliness, a contaminant concentration per surface area and/or a particulate count may be calculated. If the calculation reveals that the surface is acceptably clean, the surface may be placed in a contaminant sensitive environment, such as an oxygen facility or an environment that allows the surface to be placed in contact with a halogen such as fluorine. In addition or in the alternative, the surface may be bonded to another surface, e.g., one that comprises epoxy.

Additional embodiments of the invention will be apparent from the disclosure contained herein.

BRIEF DESCRIPTION OF THE DRAWINGS

The invention and aspects thereof shown in the figures may not necessarily be depicted to scale, and certain dimensions may be exaggerated for clarity of presentation.

DETAILED DESCRIPTION OF THE INVENTION

Definitions and Overview

Before describing the invention in detail, it must be noted that, as used in this specification and the appended claims, the singular forms "a," "an," and "the" include plural referents unless the context clearly dictates otherwise. Thus, for example, reference to "a contaminant" includes one or more contaminants, reference to "a parameter relevant to bondability" includes a single parameter relevant to bondability as well as a collection of parameters relevant to bondability, reference to "a wavelength" includes a single wavelength as well as a range of wavelengths, and the like.

In describing and claiming the present invention, the following terminology will be used in accordance with the definitions set out below.

The term "black light" as used herein refers to radiation invisible to the naked human eye, typically of ultraviolet (UV) or infrared (IR) wavelengths, that causes fluorescent materials to emit radiation of a different wavelength, e.g., visible light. In certain specific instances, black light refers to radiation emitted by economical gas light bulbs having a peak intensity wavelength of about 366 nm radiation, which, as discussed Chawla, cannot be used to detect machine oil.

The term "cleanliness" as in a "surface's cleanliness relative to a contaminant" is used in its ordinary sense, and refers the surface's freedom from the contaminant, e.g., foreign matter or pollution. As a related matter, the term "contaminant" as in "surface contaminant" is also used in its ordinary sense and refers to matter that renders the surface impure or unclean by its presence or contact.

The terms "fluorescence" and "fluorescent radiation" are used herein in their ordinary sense and refer to the emission of electromagnetic radiation produced by a substance as a consequence of the absorption of incident (interrogating) radiation and persisting only a short time after the incident radiation ceases to stimulate the substance. Unlike "reflected" or "transmitted" fluorescent radiation typically has a longer wavelength than its corresponding incident radiation.

The terms "phosphorescence" and "phosphorescent radiation" are used herein in their ordinary sense and refer to the emission of electromagnetic radiation produced for some time following exposure to and removal of incident (interrogating) radiation, typically at a temperature below that of incandescence.

In general, the invention provides devices and methods for quantifying a surface's cleanliness relative to a contaminant. The invention operates by using radiation to which the contaminant is responsive to interrogate the surface whose cleanliness is to be quantified or to interrogate a surface cleaner that may hold contaminant from the surface. In response to the interrogating radiation, the contaminant may produce a detectable response, e.g., fluorescent or phosphorescent radiation, which may be detected and converted into a signal. The signal is then compared to an electronic standard that corresponds to the surface in an acceptably clean state so as to quantify the surface's cleanliness.

In some instances, the invention may take the form of a hand-held field-portable instrument that is able to quickly and easily read contamination levels traceable to precision cleaning standards, e.g., U.S. Military Standard MIL-STD-1246C promulgated by the U.S. Department of Defense. Such instruments may provide readings for both the molecular contamination level, such as organic matter in the form of hydrocarbon oils, grease, etc., and particulate contamination level, such as grit and dust. Such instruments may further measure surface conditions, e.g., surface roughness, that may be relevant to surface bondability.

The invention may employ one or a combination of various optical techniques. For example, the invention may exploit the fluorescent and/or phosphorescent behavior of contaminants by employing interrogating radiation of appropriate ultraviolet (e.g., UV-A, UV-B, UV-C, etc.), visible, and/or infrared (e.g., near IR, short-wavelength IR, mid-wavelength IR, long-wavelength IR, Far IR, etc.) wavelengths. Such interrogating radiation may exhibit a range of wavelengths or be monochromatic in nature. As another example, the invention may exploit the fact that particulate contaminants scatter light, and a detector may be used that is responsive to reflected or transmitted radiation. By comparing signals associated with light scattering to signals associated with no light scattering, particulate matter may be quantified. As a further example, any of these techniques can be supplemented with variations on illumination (frontal illumination, edge illumination, blue, etc.). In any case, exemplary detectors that may be used with the invention include CCD arrays, miniature spectrometers, photodiodes, microelectronic devices, and the like. Optionally, devices of the invention may include an interface or so that data gathered by the analyzer may be transferred to remote computers.

The invention may be practiced via in situ measurements. In situ measurements, for example, may involve placing the inventive instrument such that the interrogating radiation is directed toward the surface whose cleanliness is to be quantified. In such a case, spectrometer may be used to quantify molecular contamination via fluorescent intensity. In addition or in the alternative, the detector may comprise a camera or other type of imaging technology suitable for counting particulates. Care must be taken to distinguish signals generated by the surface versus signals generated by contaminants.

Standard contamination tests may be adapted for use with the invention. One standard contamination test involves wiping a region of a predetermined area, e.g., one square foot, of the surface with a high-quality filter paper as a surface cleaner and sending the filter paper for NVR testing. Another standard test involves rinsing the surface in a surface cleaner in the form of a solvent, e.g., haloalkanes sold by DuPont under the trademark Freon®, and analyzing the surface cleaner via remote NVR testing. In either case, the inventive device may be constructed for on-site testing so as to supplement or replace remote NVR testing. Such devices may, for example, include surface cleaner holder constructed to hold a sheet of filter paper or a rinse fluid.

Once a surface is determined to be acceptably clean, the surface is may be ready for use. For example, the surface placed in a contaminant sensitive environment. As discussed above, the invention is particularly suited to determine whether a surface is sufficiently clean for exposure to oxygen facilities or for contact with a halogen such as fluorine. In addition, the surface may be bonded to another surface, e.g., an epoxy surface.

Contaminant Quantification

The invention employs optical means that generally conform to accepted standards of the precision cleaning industry to quantify the cleanliness of a surface. In particular, the invention employs optical technologies that represent an improvement over black-light detection practices known in the precision cleaning industry. Accordingly, some background regarding how black-light detection practices are carried out is warranted.

As alluded to above, black light has been used to provide a qualitative indication of the cleanliness of a surface. For example, known surface cleaning protocols typically involve first wiping a predetermined area of the surface with a standard two-inch diameter scientific grade filter paper. Then, the filter paper is exposed to UV radiation. If the paper is observed to exhibit fluorescence, i.e., by glowing while exposed UV radiation, additional cleaning is needed.

For certifiable results, the paper is typically sent to a specialized lab for NVR testing to quantify how much nonvolatile residue was removed from the surface. NVR testing may involve rinsing the paper with a solvent to remove contaminants therefrom and quantifying contaminants in the run-off solvent. The results of NVR testing may then be used to determine whether the surface exhibits a cleanliness level that conforms to an accepted standard of cleanliness.

Considering how inaccurate human eyes are as optical instruments, that the qualitative test may serve as an initial screening technique at all is impressive. Human eyes, for example, have greatly varying sensitivity both between day and night vision and between one person and the next. Further, certain important fluorescence phenomena occurs at the blue edge of the visible spectrum and naked-eye sensitivity at either edge of visible light varies greatly from one individual to another. In short, naked-eye black-light inspection as a protocol is fraught with variability due to is subjective and qualitative nature.

In contrast, the invention provides, as an inventive embodiment, an optical instrument capable of performing quantitative black-light analysis and of creating a record that is analyzable relative to accepted electronic standards. Unlike human eyes, photodetectors are consistent and quantitative. The inventive instrument may be used to make measurements of fluorescence and, using a calibration curve, report the contamination level to the user. In addition, the fluorescence spectra of the contaminants can be quantified, leading to identification of individual contaminant species. With the addition of more excitation sources, covering the wavelength spectrum from blue to UV-A, further discrimination among contaminant species would be possible.

The accuracy the invention may be independently verified using known techniques, e.g., via NVR testing techniques. For example, the invention may be used first to quantify a surface's cleanliness by directly interrogating the surface. Then, the surface may be wiped with filter paper, and the invention may be used to quantify the cleanliness of filter paper. In turn, the paper may be sent for NVR testing to verify the result obtained by the practice of the invention. In this way, the accuracy and precision of the invention may be calibrated and/or verified using industry standards.

Figure 1:
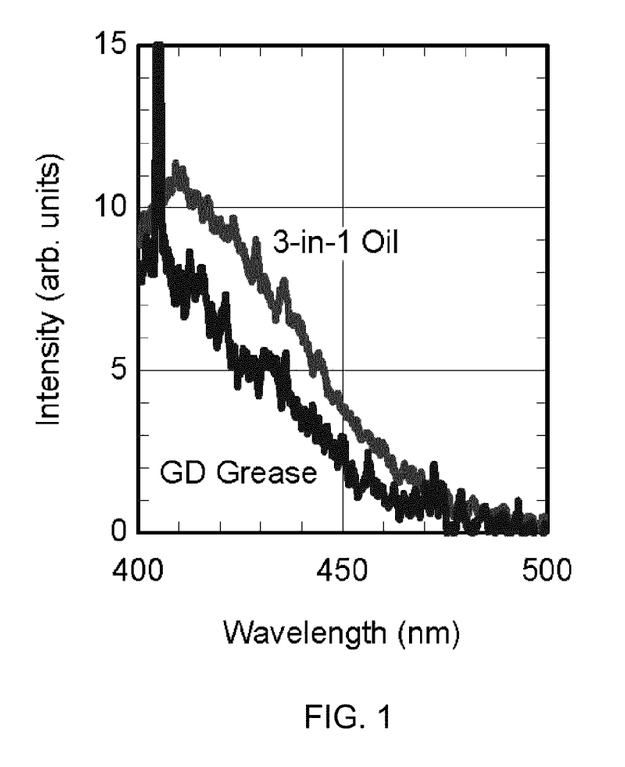
FIG. 1 graphically illustrates differences in fluorescence behavior of common organic contaminants, i.e., 3-in-1 oil and household (garage door) grease, under UV light generated by a mercury lamp. The peak at 405 nm is from the mercury lamp.

To demonstrate the feasibility of such an approach the fluorescence spectra of two different hydrocarbon contaminants were measured. A long-wave black-light lamp was used to illuminate filter paper specimen from Whatman Inc. (Piscataway, N.J.) holding different contaminants. One specimen was contaminated with 3-in-1 (SAE-20) oil, and another was contaminated with a common household (garage door) grease. A detector was used to collect fluorescence spectra and the output was plotted. The fluorescence spectra are shown in FIG. 1.

As expected, the fluorescence yields of the contaminants were fairly similar. Both glow at the blue end of the visible spectrum. This is not surprising because oils and greases typically belong to the hydrocarbon family and have similar chemical structure. There are significant differences, however. For example, the oil appears to peak at a longer wavelength than the grease. The human eye could never detect such a difference. Such difference may be exploited to help improve the calibration of the analyzer and, possibly, to distinguish different types of identify the contaminants.

The invention may also be used to quantify particulate contaminants. This can be done using any of the sampling methods described above. For example, particulates may be spread out on a surface, illuminated, and imaged (e.g., via CCD camera). Then, software may be used to provide a particle count.

Optionally, the particles may be sized. Large particle can be sized by determining the number of pixels needed to capture their entireties. Small particles can be sized by intensity of light they reflect. The relationship between intensity and size can be established by using commercially available particles of known size as a calibration standard. For example, spherical microparticles with calibrated sizes traceable to the National Institute of Standards and Technology (NIST) are available from Thermo Fisher Scientific Inc. (Waltham, Mass.), formerly Duke Scientific.

Certain techniques may be used to enhance particle quantification. For example, edge illumination techniques may serve to highlight the particle for counting and/or counting, even if the particles are the same color as the surface on which they lie. Regardless of color, a particle will scatter light due to irregular discontinuities in the index of refraction that characterize a particle as opposed to a clean surface.

Other illumination methods can also be used to advantage as well. For example, illumination with different wavelengths can help determine the particles composition. When exposed to UV radiation, organic particles may fluoresce.

Exemplary Instrumentation

Figure 2:
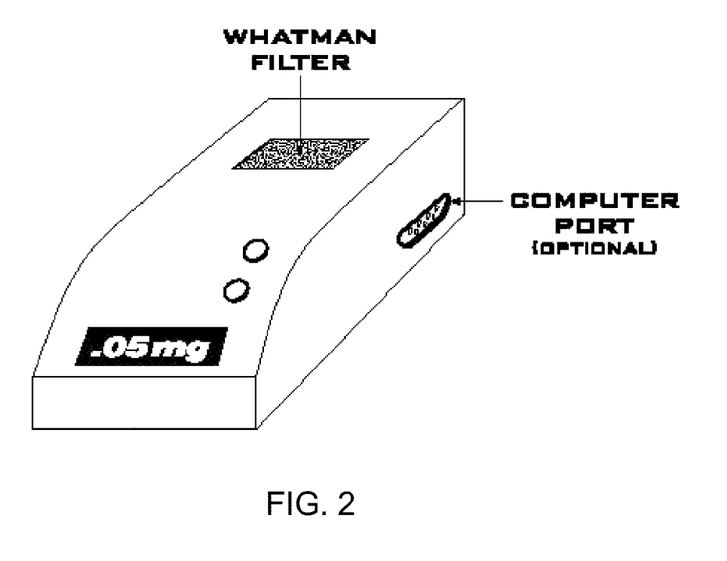
FIG. 2 depicts an exemplary embodiment of the invention in the form of a small hand-held instrument that can quantitatively read fluorescence under black light.

In certain embodiments, the invention may provide a small hand-held battery-powered instrument. FIG. 2 depicts an exemplary embodiment of the invention in the form of a small hand-held battery powered instrument that can quantitatively read fluorescence under black light. Optionally, the battery (not shown) may be replaced or supplemented with an AC power supply. As shown, the instrument houses a sample cleaner holder adapted to a piece of Whatman filter paper, a display the shows analytical results in units of mass, and an optional computer port.

Figure 3:
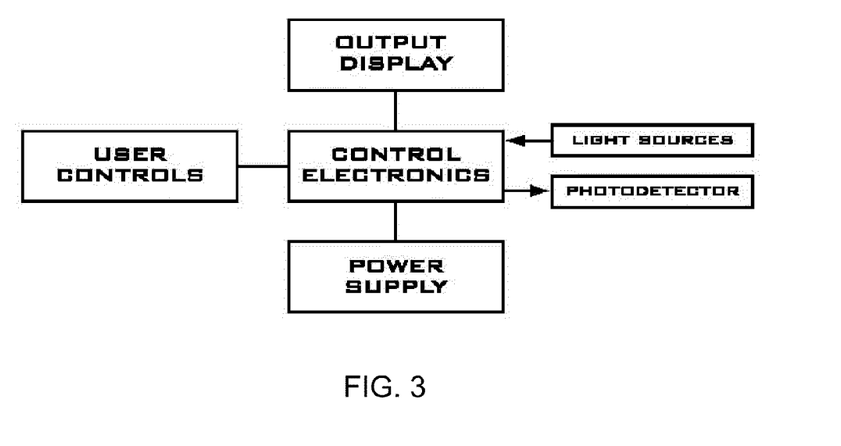
FIG. 3 shows a block diagram of an exemplary instrument of the invention.

FIG. 3 shows a block diagram the instrument depicted in n FIG. 2. User controls may be interfaced with control electronics, which communicate electrically with the output display and a power supply. The operation of control electronics may be triggered in part by the activation of interrogating radiation sources, which, in turn, may activate the photodetector.

Figure 4:
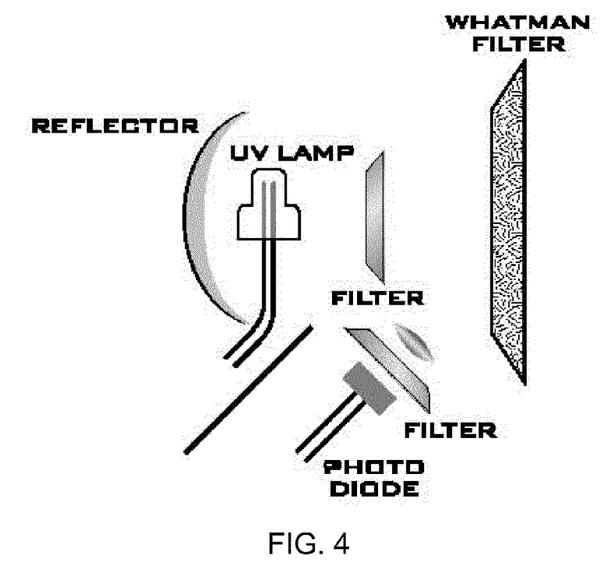
FIG. 4 shows in schematic view an exemplary setup in which a UV light source is used to illuminate a contaminated specimen of Whatman filter paper, and a photodiode is used to detect fluorescence produced as a result.

FIG. 4 shows in schematic view an exemplary setup in which a UV light source is used to illuminate a contaminated specimen of Whatman paper and a photodiode is used to detect fluorescence produced as a result. The setup is particularly suited for quantifying molecular contaminants. As shown, the UV light source may take the form of a mercury lamp in combination with a reflector that serves to direct the radiation from the mercury lamp toward the specimen. An optical filter is interposed between the lamp and the specimen so that visible light is prevented from reaching the specimen. Once the filtered UV light reaches the specimen, contaminants held thereby may exhibit fluorescent behavior. Any fluorescent radiation produced may be collected by a lens and quantified by a photodiode. Optionally, reflected and other stray UV radiation may be blocked from reaching the photodiode by a UV-blocking filter interposed between the specimen and the photodiode. An additional photodiode (not shown) may be used to measure the UV intensity of the lamp for purposes of calibration.

It should be noted that the invention is not limited to black-light radiation technologies, as described in Chawla in which black-light sources are used having a peak intensity wavelength of about 366 nm. Commercially available technology has improved to the point that, mercury lamps, properly powered and filtered, are now also capable of emitting at 253.65 nm and several other wavelengths. This enables clear observation of many contaminants that were previously thought at the time of Chawla unobservable with black-light techniques. Modern LED sources offer many choices with emission peaks from 250 nm to 400 nm.

Figure 5:
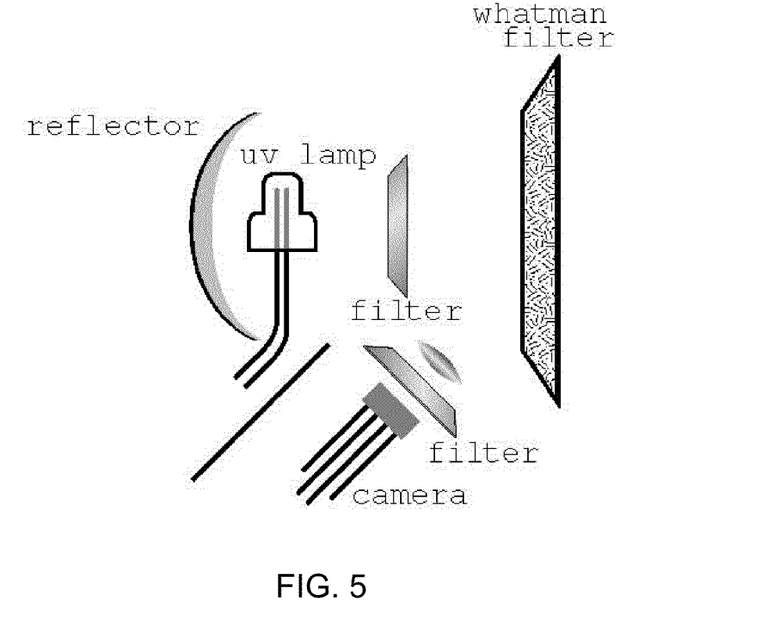
FIG. 5 shows in schematic view a variant of the setup shown in FIG. 4 in which the photodiode is replaced by a CCD camera.

As discussed above, a CCD (or CMOS) camera may be used to image particulate contamination. A series of images may be taken under different illumination schemes. These images may then be analyzed by a microprocessor to count and/or size particles. As shown in FIG. 5, a variant of the setup shown in FIG. 4 may be used to carry out such particle quantification. Persons of ordinary skill in the art would recognize that the invention may employ a detection scheme that employs both photodiodes and CCD cameras to quantify both molecular and particulate contaminants.

As discussed above, spectral information obtained through the use of the invention may be employed in a calibration context and/or to help type of contaminant. In some instances, quasi-spectral information may be obtained by employing multiple photodiodes, each with a different spectral filter or a photodiode array with a linear variable filter. More complete spectral information may be obtained by using miniature spectrometer as the detector of the invention. In either case, quantitative measurements of fluorescence may be made at different wavelengths. The ratios of the intensities at the different wavelengths could be correlated contaminant composition. The difference in the spectra of different hydrocarbon compounds shown in FIG. 2 indicates the potential for this approach.

Further information may be obtained from the decay times of the fluorescent or phosphorescent radiation. Thus, in some embodiments, it may be preferred that the invention employ one or more light sources with rapid response performance capabilities, e.g., with capability for rapid turn on and turn off. This has two advantages. First, since sensitivity to minute quantities of contamination is important, the use of lock-in amplifier techniques can help improve signal-to-noise ratio and hence sensitivity. This typically optimizes at a flashing rate of 1 kHz to 50 kHz. Secondly, if the light source turns off quickly, it is possibly to measure or infer the fluorescent or phosphorescent decay time of the contaminant. This can contain information about the type of contaminant and/or its environment. This usually requires turn-off times of no more than a microsecond or, equivalently, on-off flashing rates of megahertz and above.

Furthermore, infrared spectroscopic techniques may also be used to improve the quantitative aspects of invention. It is well known that infrared spectroscopy techniques have been likened to a "molecular fingerprinting." Traditional infrared analysis has required expensive instruments, special windows, and cryogenic cooling. Recent advances in semiconductor technology, however, enable practical affordable instruments using conventional optical materials that perform spectroscopy (at room temperature) in the near-infrared. Commercially packaged miniature spectrometers are now available in for near-IR applications.

Figure 6:
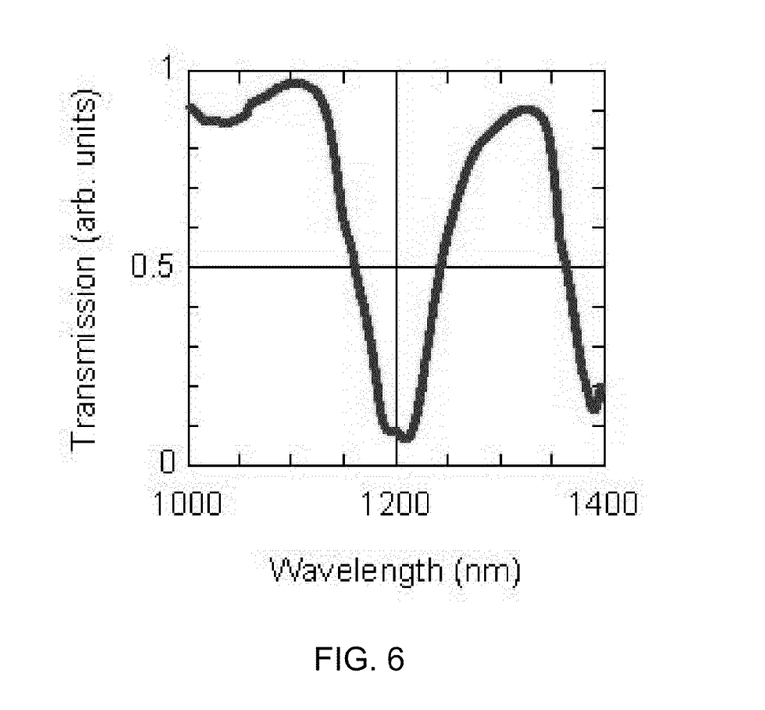
FIG. 6 graphically illustrates the transmission of the IR spectrum for 3-in-1 oil as plotted against wavelength FIG. 7 graphically illustrates the near-IR reflection spectrum of a specimen of oil-contaminated filter paper relative to the reflection spectrum of a clean (uncontaminated) specimen.

To illustrate the nature of near-IR technology, experiments were performed on a sample of pure 3-in-1 (SAE 20) motor oil, a typical repair shop contaminant. Light transmission was measured through the oil. FIG. 6 graphically illustrates transmission spectra of the 3-in-1 oil sample as plotted against wavelength. Notably, the oil sample shows strong absorption (low transmission) behavior near 1200 nm and 1400 nm. These absorption peaks (among others not shown) are common to petroleum products ranging from oils to gasolines. By studying the precise shapes and relative heights of the peaks, it is possible to determine nearly all properties of oil or gasoline from viscosity to cloud point.

Figure 7:
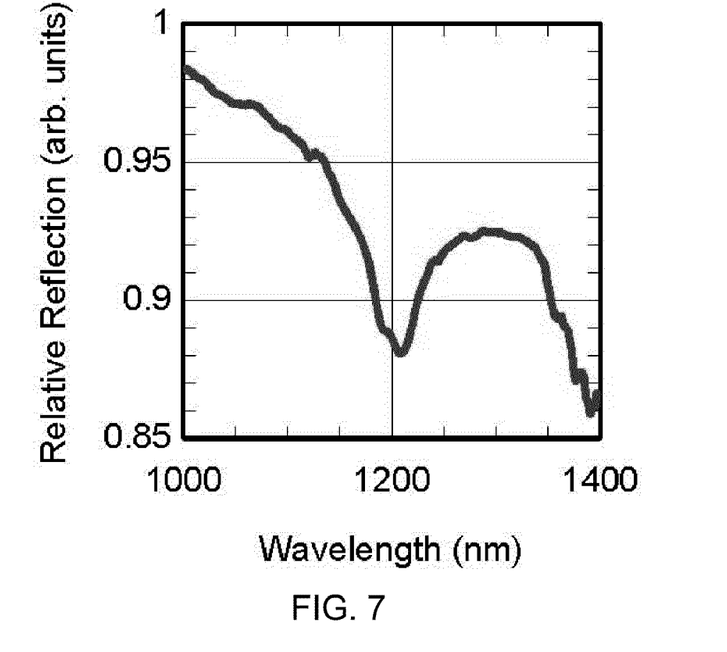

To see whether the invention may be applied to bondability applications, reflected near-IR radiation from a Whatman filter paper specimen was measured under both clean and contaminated conditions. 3-in-1 oil was used as the contaminant. As shown in FIG. 7, the contaminant oil reduced reflected radiation at several wavelengths. The spectral features at 1200 nm and 1400 nm match those of the pure oil. In particular, the spectral feature at 1200 nm regions exhibits a double peak with one peak a little stronger than the other. A similar double peak can also be seen for the spectral plot at 1200 nm for pure oil in FIG. 6. Accordingly, it is clear that the invention may be used to quantify oil contamination a Whatman filter using near infrared spectroscopy.

Figure 8:
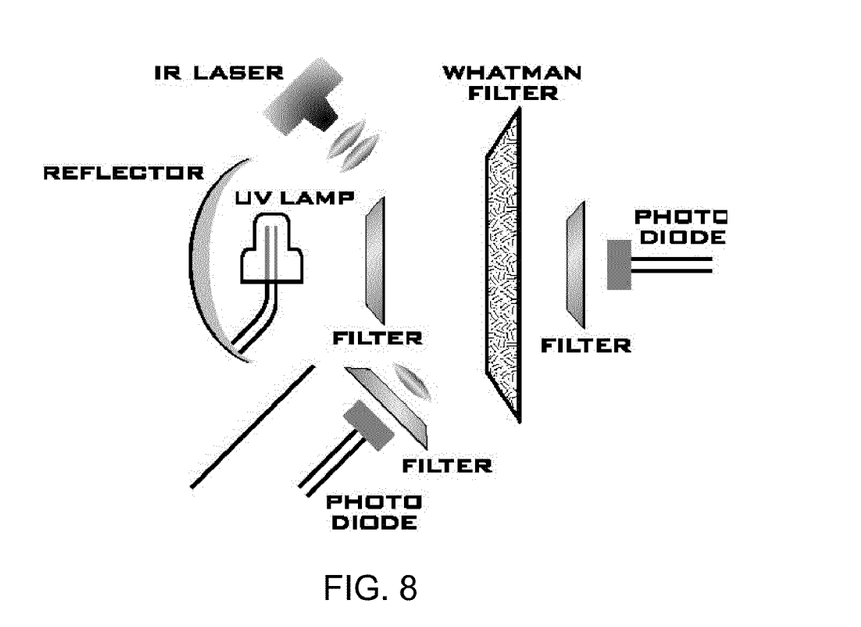
FIG. 8 shows in schematic view a variant of the setup shown in FIG. 4 in which an IR laser and an additional photodiode are added to provide improve accuracy.
Figure 9:
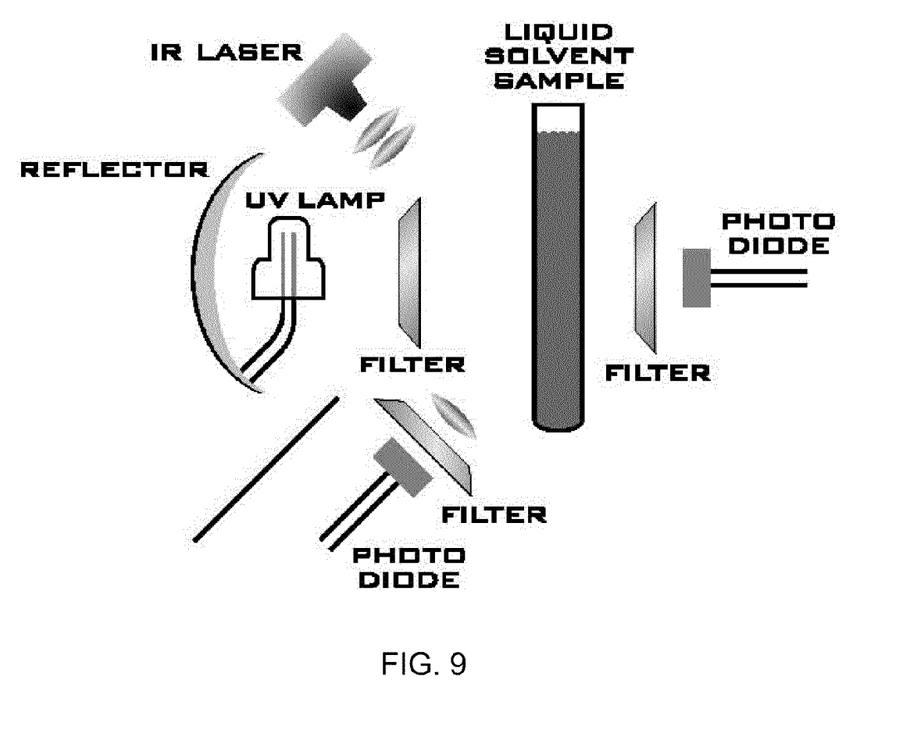
FIG. 9 shows in schematic view a variant of the setup shown in FIG. 8 except that the paper specimen has been replaced with a liquid solvent sample.

Certain infrared technology may be used to enhance in the inventive instrument. For example, FIG. 8 shows in schematic view a variant of the setup shown in FIG. 4 in which an IR laser and an additional photodiode are added to provide improve accuracy. The setup operates in a manner similar to that depicted in FIG. 4 except that the IR laser and additional photodiode may be used to carry out spectroscopic measurements to supplement the fluorescence quantification capabilities of the invention. In some instances, the laser may be tuned over its wavelength range to obtain spectral information that may distinguish further the different kinds of contaminants. For example, near-IR spectra may be used to infer viscosity or SAE number FIG. 9 shows in schematic view a variant of the setup shown in FIG. 8 except that the paper specimen has been replaced with a liquid solvent sample. Such a setup may be used in rinse testing applications. More specifically, smaller parts or rough surfaces having a form factor unfriendly to wiping may benefit from such a setup. With this setup, blacklight fluorescence may be measured directly from the solvent wash and while a CCD camera inspects for particles in the solvent Thus, the invention represents a novel and nonobvious improvement to cleaning protocols that require sending samples to a specialized laboratory and waiting days for results, e.g., "NVR testing." In some embodiments, portable field instrumentation may be provided for quantifying a surface's cleanliness in a near instantaneous manner. Such instrumentation may be used to facilitate repairs on aircraft in hangers at airports or other uncontrolled environments, where the use of clean rooms or specially trained technicians is not practical.

In addition, the invention also represents a novel and nonobvious improvement to cleaning techniques requiring qualitative naked eye observations. For example, a typical young person can see a black lit 50 µm particle with the naked eye while an older person can see a 100 µm particle. With optics means as described above, even small hand-held instruments can routinely read particles down to 0.3 µm or smaller.

It will be apparent to those of ordinary skill in the art that the invention may be embodied in various forms and that the invention. In addition, it is to be understood that while the invention has been described in conjunction with the preferred specific embodiments thereof, that the foregoing description is intended to illustrate and not limit the scope of the invention. Aspects of different embodiments of the invention may be included or excluded from other embodiment. Other aspects, advantages and modifications within the scope of the invention will be apparent to those skilled in the art to which the invention pertains.

All patent applications and patents mentioned herein are hereby incorporated by reference in their entireties to an extent not inconsistent with the above.

What is claimed is:

1. A device for quantifying a surface's cleanliness relative to at least one contaminant, comprising:
 a source of interrogating radiation to which the at least one contaminant on a surface is responsive;
 a means for directing the interrogating radiation toward a nonmetallic article, the nonmetallic article having the surface or comprising a surface cleaner that may hold the at least one surface contaminant from the surface;
 a detector positioned to detect radiation from the nonmetallic article produced in a fluorescent and/or phosphorescent manner in response to the interrogating radiation by the at least one contaminant, and adapted to generate a signal that corresponds to the detected radiation;
 an analyzer for quantifying the surface's cleanliness, the analyzer constructed to compare the signal relative to an electronic standard that corresponds to the surface being in an acceptably clean state for exposure to a chemically reactive environment and/or for application of an adhesive for bonding to another article.

2. The device of claim 1, wherein the at least one contaminant comprises particulate matter.

3. The device of claim 1, wherein the at least one contaminant comprises organic matter.

4. The device of claim 3, wherein the organic matter is a hydrocarbon.

5. The device of claim 1, wherein the source of interrogating radiation emits ultraviolet radiation.

6. The device of claim 1, wherein the emitted ultraviolet radiation has a peak intensity wavelength shorter than about 350 nm.

7. The device of claim 1, wherein the source of interrogating radiation emits infrared radiation.

8. The device of claim 1, wherein the source of interrogating radiation emits visible light.

9. The device of claim 1, wherein the interrogating radiation is monochromatic.

10. The device of claim 1, wherein the interrogating radiation includes a range of wavelengths.

11. The device of claim 1, further comprising a surface cleaner holder.

12. The device of claim 11, wherein the surface cleaner holder is constructed to hold a sheet of filter paper.

13. The device of claim 1, wherein the surface cleaner holder is constructed to hold a fluid that may include the at least one contaminant from the surface.

14. The device of claim 1, wherein the detector is responsive to fluorescent radiation from the surface or the surface cleaner.

15. The device of claim 1, wherein the detector is responsive to phosphorescent radiation from the surface or the surface cleaner.

16. The device of claim 1, wherein the detector is further responsive to reflected radiation by the surface or the surface cleaner.

17. The device of claim 1, wherein the detector is further responsive to transmitted radiation by the surface or the surface cleaner.

18. The device of claim 1, wherein the detector includes a CCD and/or CMOS camera.

19. The device of claim 1, wherein the detector includes a photodiode.

20. The device of claim 1, wherein the analyzer comprises a microelectronic device.

21. The device of claim 1, wherein the analyzer has a computer port interface.

22. The device of claim 1, wherein the device is handheld.

23. The device of claim 1, further comprising a means for measuring a parameter relevant to bondability.

24. The device of claim 23, wherein the bondability parameter is the surface's roughness.

25. The device of claim 1, wherein the analyzer comprises a calculator for calculating a contaminant concentration per surface area.

26. The device of claim 1, wherein the analyzer comprises a calculator for calculating a particulate count.

27. The device of claim 1, wherein the nonmetallic article comprises epoxy, a composite material, and/or paper.

28. The device of claim 27, wherein an electronic standard that corresponds to the surface being in an acceptably clean state for application of an adhesive for bonding to another article.

29. The device of claim 27, wherein an electronic standard that corresponds to the surface being in an acceptably clean state for exposure to a chemically reactive environment.

* * * * *